United States Patent [19]

Livingston et al.

[11] Patent Number: 5,262,321
[45] Date of Patent: Nov. 16, 1993

[54] DNA ENCODING P107 TUMOR SUPPRESSOR

[75] Inventors: David M. Livingston; Mark E. Ewen, both of Brookline, Mass.

[73] Assignee: Dana-Farber Cancer Institute, Boston, Mass.

[21] Appl. No.: 708,962

[22] Filed: May 31, 1991

[51] Int. Cl.$^5$ ............. C12N 15/12; C12N 15/70; C12N 1/21; C12N 5/10
[52] U.S. Cl. ............. 435/240.2; 435/252.3; 435/252.33; 536/23.5
[58] Field of Search ............. 435/6, 172.3, 252.33, 435/240.2; 536/27, 23.5

[56] References Cited

FOREIGN PATENT DOCUMENTS

0259031A3  3/1988  European Pat. Off. .
0390323A2  10/1990 European Pat. Off. .

OTHER PUBLICATIONS

Ewen, et al., "An N-Terminal Transformation-Governing Sequence of SV40 Large T Antigen Contributes to the Binding of Both p110Rb and a Second Cellular Protein, p120", Jul. 28, 1989, *Cell*, vol. 58, pp. 257-267.
Whyte, et al., "Cellular Targets for Transformation by the Adenovirus E1A Proteins", Jan. 13, 1989, *Cell*, vol. 56, pp. 67-75.
Harlow, et al., "Association of Adenovirus Early-Region 1A Proteins with Cellular Polypeptides", May, 1986, *Molec. and Cell. Biol.*, vol. 6, No. 5, pp. 1579-1589.
Dyson et al. (1989), Cell 58: 249-255.
Jacobs et al. (1985), Nature 313: 806-810.

*Primary Examiner*—Richard A. Schwartz
*Assistant Examiner*—Philip W. Carter
*Attorney, Agent, or Firm*—Choate, Hall & Stewart

[57] ABSTRACT

A cDNA encodes p107; a cell contains recombinant p107-encoding DNA; and substantially all of the cells of a nonhuman mammal contain recombinant p107-encoding DNA. Also, a method for diagnosing a condition of tumorigenicity in a subject, includes the steps of obtaining a tissue sample from the subject and detecting the presence of non wild-type p107-encoding gene in the sample, or detecting the absence of wild-type p107-encoding gene in the sample; or extracting DNA from the sample and detecting the presence of non wild-type p107-encoding gene or the absence of wild-type p107-encoding gene in the DNA. Also, a nucleic acid probe is complementary to a portion of a human mutant p107 gene.

3 Claims, 7 Drawing Sheets

```
  1 GTAATATTCAAAAATATGAGCCAATTTTTTTAGATATATTTCAAAATCCATATGAAGAACCACAAGTTACCACGAAGCCGAAGCAG
 (1)   V  I  F  K  K  Y  E  P  I  F  L  D  I  F  Q  N  P  Y  E  E  P  P  K  L  P  R  S  R  K  Q

91 AGGAGGATTCCTTGCAGTGTTAAGGATCTGTTAATTTCTGTTGGACACTTTTTGTTTATACTAAGGGTAATTTCGGATGATTGGGGAT
(31)   R  R  I  P  C  S  V  K  D  L  L  I  S  V  G  H  F  L  F  I  L  R  G  N  F  R  M  I  G  D

181 GACTTAGTAAACTCTTATCATTACTTCTATGCTGCTTGGATCTGCTTGATTTTGCCAATGCGATTATGTGCCCAAATAGACAAGACTGCTA
(61)   D  L  V  N  S  Y  H  L  L  C  C  L  D  L  I  F  A  N  A  I  M  C  P  N  R  Q  D  L  L

271 AATCCATCATTAAAGGTTTACCATCTGATTTCATACTGCTGACTTACGGCTTCTGAAGAGCCACCCTGCATCATTGCTGTACTGTGT
(91)   N  P  S  F  K  G  L  P  S  D  F  H  T  A  D  F  T  A  S  E  E  P  P  C  I  A  V  L  C

361 GAACTGCATGATGGACTTCTCGTAGAAGCAAAAGGAATAAAGGAGCACTACTTTAAGCCATATATTTCAAAACTCTTTGACAGGAAGATA
(121)  E  L  H  D  G  L  L  V  E  A  K  G  I  K  E  H  Y  F  K  P  Y  I  S  K  L  F  D  R  K  I

451 TTAAAAGGAGAATGCCTCCTCGACCTTTCAAGTTTTACTGATAATAGCAAAGCAGTGAATAAGGAGTATGTTCTAACTGTT
(151)  L  K  G  E  C  L  L  D  L  S  S  F  T  D  N  S  K  A  V  N  K  E  Y  V  L  T  V

541 GGTGATTTTGATGAGAGGATCTTTTTGGGAGCAGACGCCAGAGACGAAGAGGAAATTGGAACACCTCGAAAGTTCACTCGTGACACCCCCATTAGGG
(181)  G  D  F  D  E  R  I  F  L  G  A  D  A  E  E  E  I  G  T  P  R  K  F  T  R  D  T  P  L  G

631 AAACTGACAGCACAGGCTAATGTGGAGTATAACCTTCAACAGCACTTTGAAAAAAAGGTCATTTGCACCTTCTACCCCACTGACCGGA
(211)  K  L  T  A  Q  A  N  V  E  Y  N  L  Q  Q  H  F  E  K  K  R  S  F  A  P  S  T  P  L  T  G

721 CGGAGATATTTACGAGAAAAAGAAGCAGTCATTACTCCCTGTTGCATCAGCAAAGTGTGAGCCGGTTACAGAGTATTGTGGCTGGT
(241)  R  R  Y  L  R  E  K  E  A  V  I  T  P  V  A  S  A  T  Q  S  V  S  R  L  Q  S  I  V  A  G

811 CTGAAAAATGCACCAAGTGACCAACTTATAAATATTTTGAATCTTGTGTGCGTAATCCTGTGGAAAAACATTATGAAAATACTAAAAGGA
(271)  L  K  N  A  P  S  D  Q  L  I  N  I  F  E  S  C  V  R  N  P  V  E  N  I  M  K  I  L  K  G
```

FIG. 1.1

```
 901  ATAGGAGACTTTCTGTCAACACTATACTCAATCAACAGATGAACAGCCAGGATCTCACATAGACTTTGCTGTGTAAACAGACTAAAGCTG
(301)  I  G  E  T  F  C  Q  H  Y  T  Q  S  T  D  E  Q  P  G  S  H  I  D  F  A  V  N  R  L  K  L

991  GCAGAAATTTGTATTATAAATACTAGAGACTTGTAATGGTTCAGGAAACACGAAGACTTCATGGAATGTCTCTTTGCTCTCTTTGCCTATAGCTCACCTCGTACTTTCCTTGATTATT
(331)  A  E  I  L  Y  K  I  L  E  T  V  M  V  Q  E  T  R  R  L  H  G  M  D  M  S  V  L  L  E

1081  CAAGATATATTTCATCGTGTTCCTTGATGGCTTGTGTTGTTGGAAATTGTGTCTCTTTGCCTATAGCTCACCTCGTACTTTCCTTGATTATT
(361)  Q  D  I  F  H  R  S  L  M  A  C  C  L  E  I  V  L  F  A  Y  S  S  P  R  T  F  P  W  I  I

1171  GAAGTTCTCAACTGCAACCATTTACTTTTATAAGGTTATTGAGGTGGTGATCCGCTCAGAGAGGGCTCTCAAGGACATGGTGAAA
(391)  E  V  L  N  L  Q  P  F  Y  F  Y  K  V  I  E  V  V  I  R  S  E  E  G  L  S  R  D  M  V  K

1261  CACCTAAACAGCATTGAAGAACAGATTTTGGAGAGTTTAGCATGAGTCACGATTCTGCACTGTGGGAGCTCTCCAGTTTCTGCAAAC
(421)  H  L  N  S  I  E  E  Q  I  L  E  S  L  A  W  S  H  D  S  A  L  W  E  A  L  Q  V  S  A  N

1351  AAAGTTCCTACCTGTGAAGAAGTTATATTCCCAAATAACTTTGAAACAGGAGAAATGTCAGGAGGACATCTCCCCTGATGCCA
(451)  K  V  P  T  C  E  E  V  I  F  P  N  N  F  E  T  G  N  G  G  H  L  P  L  M  P

1441  ATGTCTCCTCTAATGCACCCAAGAGTCAAGACAGTGGAGTCTTCGAAGATATGCAACCATTGTCTCCAATTCT
(481)  M  S  P  L  M  H  P  R  V  K  E  V  R  T  D  S  G  S  L  R  R  D  M  Q  P  L  S  P  I  S

1531  GTCCATGAACGCTACAGTTCTCCTACGGCAGGAGTGCTAAGACCTCTTTGGAGAGGAGACCCCCAAAGGAAATGTTATGGACAAG
(511)  V  H  E  R  Y  S  S  P  T  A  G  S  A  K  R  R  L  F  G  E  D  P  P  K  E  M  L  M  D  K

1621  ATCATAACAGAAGGAACAAAATTGAAAATCGCTCCTCCTTCTTCAAGCATTACTGCTGAAAATGTATCAATTTACCTGGTCAAACTCTTCTA
(541)  I  I  T  E  G  T  K  L  K  I  A  P  S  S  I  T  A  E  N  V  S  I  L  P  G  Q  T  L  L

1711  ACAAGGCCACAGCCCCAGTAACAGGAACAACAGGACATAAGTTACACCATGGTGCGAAATGATGCTGGAGAGATCACA
(571)  T  M  A  T  A  P  V  T  G  T  T  G  H  K  V  T  I  P  L  H  G  V  A  N  D  A  G  E  I  T

1801  CTGATACCTCTTTCCATGAATACAAATCAGGAGTCCAAAGTCAAGAGTCCTGTATCACTTACTGCTCATTCATTAATTGGTGCTTCTCCA
(601)  L  I  P  L  S  M  N  T  N  Q  E  S  K  V  K  S  P  V  S  L  T  A  H  S  L  I  G  A  S  P
```

FIG. I.2

```
1891       AAACAGACCAATCTGACTAAAGCACAAGAGGTACATTCAACTGGAATAACAGGCCAAAGAGAACTGGTCCTTAGCACTATTTACAGA
(631)       K  Q  T  N  L  T  K  A  Q  E  V  H  S  T  G  I  N  R  P  K  R  T  G  S  L  A  L  F  Y  R

1981       AAGGTCTATCATTGGCAAGTGTACGCTTACTGTCCTGATGTCTAAAACTGAGTGTTCAAATGAGTTACGAAGGAAGATATGGACGTGT
(661)       K  V  Y  H  L  A  S  V  R  L  R  D  L  C  L  K  L  D  V  S  N  E  L  R  R  K  I  W  T  C

2071       TTTGAATTCACTTTAGTTCACTGTCCTGATCAGCTCCTCCTTTGTGCCTTTTATATCATGGCAAAG
(691)       F  E  F  T  L  V  H  C  P  D  L  M  K  D  R  H  L  D  Q  L  L  C  A  F  Y  I  M  A  K

2161       GTAACAAAGAAGAAGAACTTTTCAAGAAATTATGAAAGTTATCAGCCCCAAGCTAATAGTCACGTATATAGAAGTGTTCTG
(721)       V  T  K  E  E  R  T  F  Q  E  I  M  K  S  Y  R  N  Q  P  Q  A  N  S  H  V  Y  R  S  V  L

2251       CTGAAAGTATTCCAAGAGAAGTTGTGGCATATATAAAATATAAAATGATGACTTTGAATGATAGATTGTGACTTAGAAGATGCTACA
(751)       L  K  S  I  P  R  E  V  V  A  Y  N  K  N  I  N  D  D  F  E  M  I  D  C  D  L  E  D  A  T

2341       AAAACACCTGACTGTTCCAGTGGACCAGTGAAGGAGGAAAGAAGTGATCTTATAAAATTTACAATACAATATATGTAGGAAGAGTGAAG
(781)       K  T  P  D  C  S  S  G  P  V  K  E  E  R  S  D  L  I  K  F  Y  N  T  I  Y  V  G  R  V  K

2431       TCATTTGCACTGAAATACGACTTGGCAAATCAGGACCATATGATGATGGATGCTCCACCACTCTCCTTTCCACATATTAAACAACAGCCA
(811)       S  F  A  L  K  Y  D  L  A  N  Q  D  H  M  M  D  A  P  P  L  S  P  F  P  H  I  K  Q  Q  P

2521       GGCTCACCACGCGCATTCCCAGCAGCACTCCATTTATATTCCCCGCACAAGAATGGGTCAGGCCTTACACCAAGAGCGCTCTGCTG
(841)       G  S  P  R  R  I  S  Q  Q  H  S  I  Y  I  S  P  H  K  N  G  S  G  L  T  P  R  S  A  L  L

2611       TACAAGTTCAATGGCAGCCCTTCTAAGAGTTTGAAAGATATCAACAACATGATAAGGCAAGGTGAGCAGAGAACCAAGAAGCGAGTAATA
(871)       Y  K  F  N  G  S  P  S  K  S  L  K  D  I  N  N  M  I  R  Q  G  E  Q  R  T  K  K  R  V  I

2701       GCCATCGATAGTGATGCAGAATCCCCTGCCAAACGCGTCTGTCAAGAAAATGATGACGTTTTACTGAAACGACTACAGGATGTGTCAGT
(901)       A  I  D  S  D  A  E  S  P  A  K  R  V  C  Q  E  N  D  D  V  L  L  K  R  L  Q  D  V  V  S

2791       GAAAGAGCAAATCATTAA
(931)       E  R  A  N  H  @
```

FIG. 1.3

N TERMINAL HOMOLOGY

REGION 1
```
p107   40 LFNFCWTLFVYTKGNFRMIGDDLVNSYHLLLCCLD  74
          **  | *   ||   * ||||  |***|*|| ||
RB    190 VLKVSWITFLLAKGEVLQMEDDLVISFQLMLCVLD 224
```

DOMAIN A HOMOLOGY

REGION 2
```
p107  252 TPVASATQSVSRLQSIVAGLKNAPSDQLINIFESCVRNPVENIMKILKGIGETFCQHY 309
          |||      *    |  | *   ||  || |    | |  ||*|||  |*|| | **
RB    373 TPVRTVMNTIQQLMMILNSASDQPSENLISYFNNCTVNPKESILKRVKDIGYIFKEKF 430
```

REGION 3
```
p107  327 RLKLAEILYYKILETVMVQETRRLHGMDMSVLLEQDIFHRSLMACCLEIVLFAYS 381
          | ||   |    ***|  *|  ||  *  ||* |||  ||*|| ||*|* ||
RB    445 RYKLGVRLYYRVMESMLKSEEERLSIQNFSKLLNDNIFHMSLLACALEVVMATYS 499
```

REGION 4
```
p107  386 FPWIIEVLNLQPFYFYKVIEVVIRSEEGLSRDMVKHLNSIEEQILESLAWSHDSALWEALQVSANK 451
          ||||*|||   |||||||||||  | *  | |*|||| |||||  |*|||||*|||||||  | **
RB    514 FPWILNVLNLKAFDFYKVIESFIKAEGNLTREMIKHLERCEHRIMESLAWLSDSPLFDLIKQSKDR 579
```

DOMAIN B HOMOLOGY

REGION 5
```
p107  648 RPKRTGSLALFYRKVYHLASVRLRDLCLKL 677
          *|*  ||  ||*|**|||*|| *||  ||*|
RB    640 KPLKSTSLSLFYKKVYRLAYLRLNTLCERL 669
```

REGION 6
```
p107  682 ELRRKIWTCFEFTLVHCPDLMKDRHLDQLLLCAFYIMAKVTKEERTFQEIMKSYRNQPQANSHVYRSVLLK 752
          || *|||| ||| ||| * *||||||||***|  |*| | |*  | *||*  |*|    ** ||*| **|
RB    675 ELEHIIWTLFQHTLQNEYELMRDRHLDQIMMCSMYGICKVKNIDLKFKIIVTAYKDLPHAVQETFKRVLIK 745
```

REGION 7
```
p107  797 LIKFYNTIYVGRVKSFALKY 816
          *|* ***| |*|  |*|  |
RB    752 IIVFYNSVFMQRLKTNILQY 771
```

FIG. 2.1

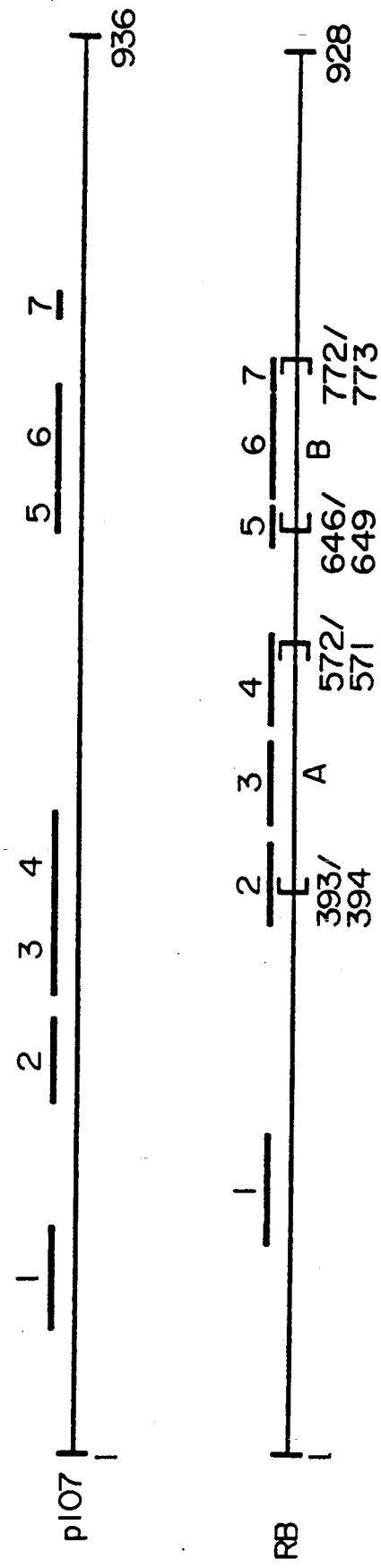
FIG. 2.2

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 2808 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
GTAATATTCA  AAAAATATGA  GCCAATTTTT  TTAGATATAT  TTCAAAATCC  ATATGAAGAA    60
CCACCAAAGT  TACCACGAAG  CCGGAAGCAG  AGGAGGATTC  CTTGCAGTGT  TAAGGATCTG   120
TTTAATTTCT  GTTGGACACT  TTTTGTTTAT  ACTAAGGGTA  ATTTTCGGAT  GATTGGGGAT   180
GACTTAGTAA  ACTCTTATCA  TTTACTTCTA  TGCTGCTTGG  ATCTGATTTT  TGCCAATGCG   240
ATTATGTGCC  CAAATAGACA  AGACTTGCTA  AATCCATCAT  TTAAAGGTTT  ACCATCTGAT   300
TTTCATACTG  CTGACTTTAC  GGCTTCTGAA  GAGCCACCCT  GCATCATTGC  TGTACTGTGT   360
GAACTGCATG  ATGGACTTCT  CGTAGAAGCA  AAAGGAATAA  AGGAGCACTA  CTTTAAGCCA   420
TATATTTCAA  AACTCTTTGA  CAGGAAGATA  TTAAAAGGAG  AATGCCTCCT  GGACCTTTCA   480
AGTTTTACTG  ATAATAGCAA  AGCAGTGAAT  AAGGAGTATG  AAGAGTATGT  TCTAACTGTT   540
GGTGATTTTG  ATGAGAGGAT  CTTTTTGGGA  GCAGACGCAG  AAGAGGAAAT  TGGAACACCT   600
CGAAAGTTCA  CTCGTGACAC  CCCATTAGGG  AAACTGACAG  CACAGGCTAA  TGTGGAGTAT   660
AACCTTCAAC  AGCACTTTGA  AAAAAAAGG   TCATTTGCAC  CTTCTACCCC  ACTGACCGGA   720
CGGAGATATT  TACGAGAAAA  AGAAGCAGTC  ATTACTCCTG  TTGCATCAGC  CACCCAAAGT   780
GTGAGCCGGT  TACAGAGTAT  TGTGGCTGGT  CTGAAAAATG  CACCAAGTGA  CCAACTTATA   840
AATATTTTTG  AATCTTGTGT  GCGTAATCCT  GTGGAAAACA  TTATGAAAAT  ACTAAAGGA    900
ATAGGAGAGA  CTTTCTGTCA  ACACTATACT  CAATCAACAG  ATGAACAGCC  AGGATCTCAC   960
ATAGACTTTG  CTGTAAACAG  ACTAAAGCTG  GCAGAAATTT  TGTATTATAA  AATACTAGAG  1020
ACTGTAATGG  TTCAGGAAAC  ACGAAGACTT  CATGGAATGG  ACATGTCAGT  TCTTTTAGAG  1080
CAAGATATAT  TTCATCGTTC  CTTGATGGCT  TGTTGTTTGG  AAATTGTGCT  CTTTGCCTAT  1140
AGCTCACCTC  GTACTTTTCC  TTGGATTATT  GAAGTTCTCA  ACTTGCAACC  ATTTTACTTT  1200
TATAAGGTTA  TTGAGGTGGT  GATCCGCTCA  GAAGAGGGGC  TCTCAAGGGA  CATGGTGAAA  1260
CACCTAAACA  GCATTGAAGA  ACAGATTTTG  GAGAGTTTAG  CATGGAGTCA  CGATTCTGCA  1320
CTGTGGGAGG  CTCTCCAGGT  TTCTGCAAAC  AAAGTTCCTA  CCTGTGAAGA  AGTTATATTC  1380
CCAAATAACT  TTGAAACAGG  AAATGGAGGA  AATGTGCAGG  GACATCTTCC  CCTGATGCCA  1440
ATGTCTCCTC  TAATGCACCC  AAGAGTCAAG  GAAGTTCGAA  CTGACAGTGG  GAGTCTTCGA  1500
AGAGATATGC  AACCATTGTC  TCCAATTTCT  GTCCATGAAC  GCTACAGTTC  TCCTACCGCA  1560
GGGAGTGCTA  AGAGAAGACT  CTTTGGAGAG  GACCCCCCAA  AGGAAATGCT  TATGGACAAG  1620
ATCATAACAG  AAGGAACAAA  ATTGAAAATC  GCTCCTTCTT  CAAGCATTAC  TGCTGAAAAT  1680
GTATCAATTT  TACCTGGTCA  AACTCTTCTA  ACAATGGCCA  CAGCCCCAGT  AACAGGAACA  1740
ACAGGACATA  AAGTTACAAT  TCCATTACAT  GGTGTCGCAA  ATGATGCTGG  AGAGATCACA  1800
CTGATACCTC  TTTCCATGAA  TACAAATCAG  GAGTCCAAAG  TCAAGAGTCC  TGTATCACTT  1860
ACTGCTCATT  CATTAATTGG  TGCTTCTCCA  AAACAGACCA  ATCTGACTAA  AGCACAAGAG  1920
GTACATTCAA  CTGGAATAAA  CAGGCCAAAG  AGAACTGGGT  CCTTAGCACT  ATTTTACAGA  1980
AAGGTCTATC  ATTTGGCAAG  TGTACGCTTA  CGTGATCTAT  GTCTAAAACT  GGATGTTTCA  2040
```

-continued

```
AATGAGTTAC GAAGGAAGAT ATGGACGTGT TTTGAATTCA CTTTAGTTCA CTGTCCTGAT   2100
CTAATGAAAG ACAGGCATTT GGATCAGCTC CTCCTTTGTG CCTTTTATAT CATGGCAAAG   2160
GTAACAAAAG AAGAAGAAC  TTTTCAAGAA ATTATGAAAA GTTATAGGAA TCAGCCCCAA   2220
GCTAATAGTC ACGTATATAG AAGTGTTCTG CTGAAAAGTA TTCCAAGAGA AGTTGTGGCA   2280
TATAATAAAA ATATAAATGA TGACTTTGAA ATGATAGATT GTGACTTAGA AGATGCTACA   2340
AAAACACCTG ACTGTTCCAG TGGACCAGTG AAAGAGGAAA GAAGTGATCT TATAAAATTT   2400
TACAATACAA TATATGTAGG AAGAGTGAAG TCATTTGCAC TGAAATACGA CTTGGCGAAT   2460
CAGGACCATA TGATGGATGC TCCACCACTC TCTCCTTTTC CACATATTAA ACAACAGCCA   2520
GGCTCACCAC GCCGCATTTC CCAGCAGCAC TCCATTTATA TTTCCCCGCA CAAGAATGGG   2580
TCAGGCCTTA CACCAAGAAG CGCTCTGCTG TACAAGTTCA ATGGCAGCCC TTCTAAGAGT   2640
TTGAAAGATA TCAACAACAT GATAAGGCAA GGTGAGCAGA GAACCAAGAA GCGAGTAATA   2700
GCCATCGATA GTGATGCAGA ATCCCCTGCC AAACGCGTCT GTCAAGAAAA TGATGACGTT   2760
TTACTGAAAC GACTACAGGA TGTTGTCAGT GAAAGAGCAA ATCATTAA              2808
```

DNA ENCODING P107 TUMOR SUPPRESSOR

This invention was made in the course of work supported in part by U.S. Government funds, and the government has certain rights in the invention.

BACKGROUND OF THE INVENTION

This invention relates to regulation of tumor suppression.

Tumors form in part as a result of disturbances in the control of cell proliferation. Alteration of one or more events in the cell cycle, particularly relating to cell division and cell differentiation, can lead to loss of control of cell multiplication. Acquisition of tumorigenicity can result from genetic changes that affect such events in the cell cycle. Generally, genetic changes such as point mutations and deletions are expected to result in a loss of function, and a genetic change that leads to tumorigenicity is likely to occur in a gene that plays a role in restraining cell multiplication. Such genes are here referred to as "tumor suppressor" genes.

SV40 large T antigen ("T") can both establish and maintain a neoplastic phenotype in responsive cell populations, and can initiate a series of events that lead to tumor formation in a suitable host. Genetic analysis has revealed a correlation between specific elements of T primary structure and transforming activity. Transformation of primary and established cells by T is dependent on a short stretch of sequence extending from residues about 105 to about 114, and a number of T mutants mapping to the 105 to 114 region have been shown to be defective in transformation.

The 105 to 114 region of T bears primary sequence and predicted secondary structure homology to one of the two transformation controlling domains of the adenovirus E1A protein domain 2, and T 101 to 108 has been shown to substitute functionally for E1A domain 2.

The product "RB" of the retinoblastoma susceptibility gene RB forms a specific complex with E1A, with T, and with E7 encoded by transforming strains of human papilloma virus. RB is a known growth regulating molecule. T-RB complex formation depends on the intact nature of the 105-114 transforming controlling region. E1A-RB complex formation depends primarily on E1A domain 2. The genetics of T-RB binding and E1A-RB binding suggest that T and E1A perform their transforming functions, at least in part, by modulating the growth regulating function of RB.

Analyses of the RB structural elements which control the T or E1A binding activity of the RB protein reveal the existence of a colinear domain of about 400 residues which alone can bind both T and E1A. Moreover, this region can specifically bind to peptide replicas of the T 105-114 and E1A domain 2 sequences and not to suitable mutant derivatives of T 105-114 or E1A domain 2. This domain of the RB protein has been termed its "pocket", because it acts as a receptacle for two viral proteins which enter it with apparently high affinity. Moreover, the RB pocket is a site for mutations resulting in spontaneous loss of function in RB, resulting in derivatives which are functionally defective in vivo and unable to bind to T or E1A in vitro. These findings suggested that the "pocket" operated, at least in part, by binding one or more cellular proteins and, therefore, that RB function was, in part, to bind to and functionally modulate certain cellular proteins with which T and E1A competed for RB binding.

A set of such cellular proteins has recently been identified in an in vitro binding assay, and all bind only when the T binding function and the E1A binding function of the "pocket" is intact. These data support the hypothesis that at least part of the function of RB is to bind certain cellular proteins.

Domain 2 of E1A and the 105-114 region of T have been shown to form a specific complex with a second cellular protein, p107, and T binding both to RB and to p107 has been shown to be competed by a synthetic peptide spanning the 105 to 114 region in T.

SUMMARY OF THE INVENTION

We have discovered that p107 binds viral proteins and cellular proteins in much the same manner as does RB, and that the p107 sequence includes a binding domain, here termed the "p107 pocket", structurally and functionally similar to the RB pocket. Protein p107 is a tumor suppressor gene product, having cell cycle regulatory activity.

We have purified and characterized p107, and have obtained and fully sequenced a near full length cDNA clone of the p107 gene from human cells. Analysis of the p107 cDNA sequence and of the behavior of its in vitro translated products show that p107 contains a binding domain like the RB pocket, which can perform a T-p107 binding function and a E1A-p107 binding function.

Comparison analysis of the deduced p107 protein sequence reveals a major region of homology with RB extending over 564 residues, that includes the respective RB and p107 pockets. There is very little homology between RB and p107 outside this region. The p107 coding sequences map to 20q 11.2.

A search of protein sequence databases reveals that, like RB, p107 does not substantially resemble other proteins whose sequences are known.

In general, in one aspect, the invention features a cDNA encoding p107; and a cell containing recombinant p107-encoding DNA; and a nonhuman mammal substantially all of whose cells contain recombinant p107-encoding DNA. In preferred embodiments the cell or the mammal's cells contain recombinant wild-type p107-encoding DNA. In preferred embodiments the p107-encoding DNA encodes human p107.

In another general aspect, the invention features a method for diagnosing a condition of tumorigenicity in a subject, including the steps of obtaining a tissue sample from the subject and detecting the presence of non wild-type p107-encoding gene in the sample, or detecting the absence of wild-type p107-encoding gene in the sample.

In another general aspect, the invention features a nucleic acid probe complementary to a portion of a human mutant p107 gene.

DESCRIPTION OF THE PREFERRED EMBODIMENTS

Drawings

FIGS. 1.1–1.3 is a diagram showing the nucleic acid sequence of the nearly complete p107 cDNA and the deduced amino acid sequence of the p107 protein.

FIG. 2.1 is a schematic showing the realtive positions of seven regions of homology (numbered bars) between the RB and the p107 amino acid sequences. The mapped domains (A, B) of the RB pocket are indicated by brackets with coordinates.

FIG. 2.2 is a set of diagrams showing the amino acid sequences for the seven regions of homology shown in FIG. 2.1. Bars indicate identity and stars indicate conservative amino acid substitutions.

Figure 3:
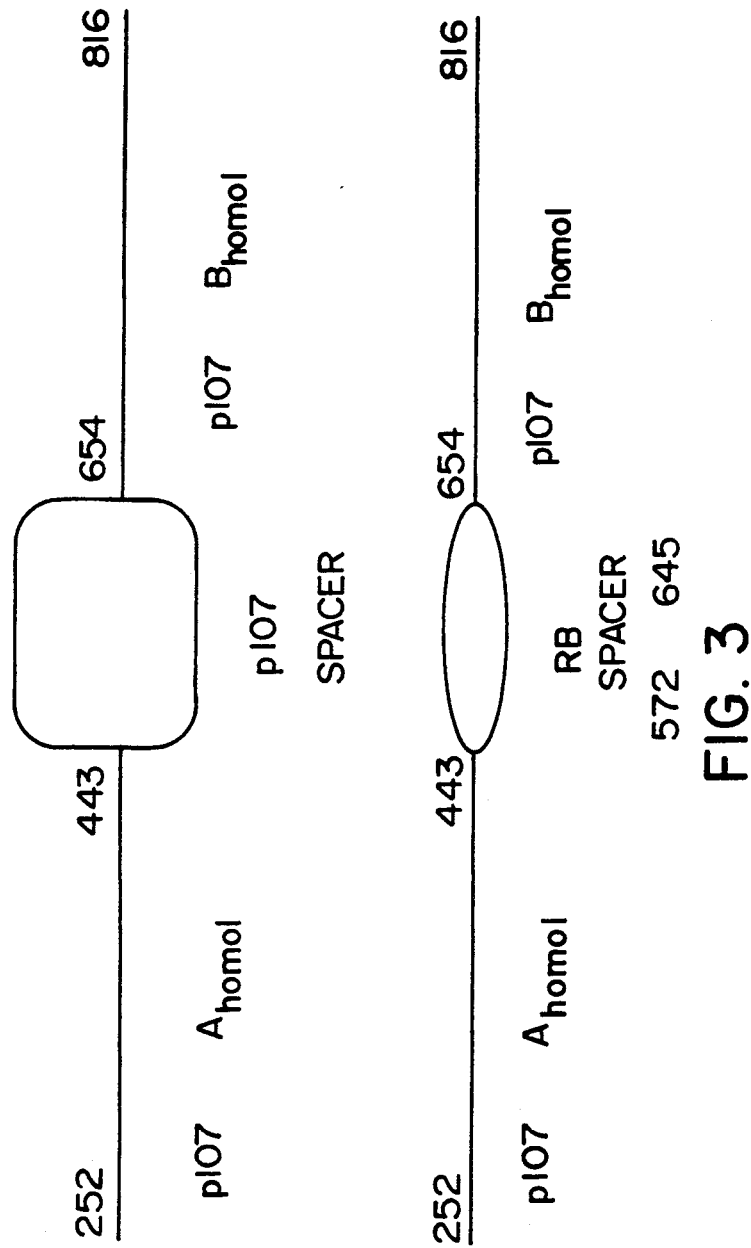

FIG. 3 is a diagram showing (upper) the native p107 pocket region and (lower) a chimeric p107 pocket region in which the RB spacer (RB residues 572-645) is substituted for the p107 spacer between the A and B regions (p107 residues 252-443, 654-816) of the p107 pocket.

Figures 4, 5:
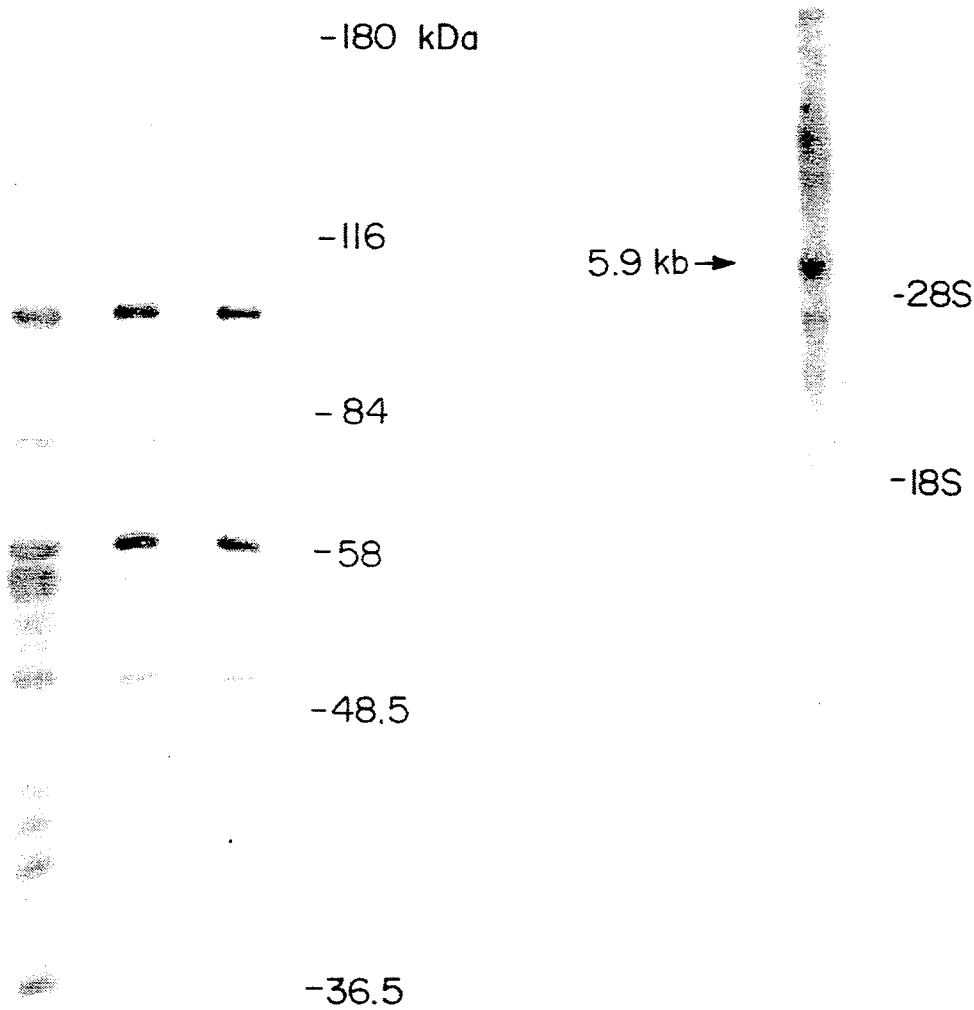

FIG. 4 is a print of a gel showing complex formation between peptide products of transcription-translation of the p107 cDNA of FIGS. 3.1-3.3 and T or E1A. Lane 1, the translation products; lane 2, an M73 immunoprecipitate of the naive translate; to test for binding, the translate was mixed with lysates prepared from: lane 3,293 cells (containing E1A); lane 4, MEFψK1 cells (containing wild-type T); lane 5, MEFψpPVU-0 cells (containing wild-type T); and immunoprecipitating with the relevant monoclonal antibody, anti-T (PAb419) or anti-E1A (M73). Complexes were separated by electrophoresis in a 7.5% SDS-polyacrylamide gel and detected by fluorography.

FIG. 5 is a print of a gel showing a northern blot of poly-A containing mRNA from 293 cells. 10 µg of poly A RNA, prepared from 293 cells was resolved in a 1% agarose-formaldehyde gel and transferred to nitrocellulose. A 2.8 kb p107 cDNA clone was $^{32}P$ labelled and served as the probe.

Structure

The near full length cDNA for the p107 gene was cloned by first obtaining an internal peptide sequence for peptide p107 and using the internal sequence to design oligionucleotides to screen a cDNA library.

In vitro translates for p107 are able to form a specific complex with viral proteins T and E1A. The peptide maps of authentic protein p107 and the in vitro p107 translate are virtually identical.

Purification of the p107 T and E1A Associated Protein

Generally, p107 was purified by immunoisolation of E1A-p107 complexes, followed by separation of the target antigen in one dimensional SDS polyacrylamide gels, as described in detail below. Briefly, an anti E1A monoclonal antibody, covalently crosslinked to protein A sepharose, was incubated with a lysate prepared from an E1A-producing human cell line, 293 ("293 cells"). The separated proteins in the gel were transferred to nitrocellulose. p107 was visualized by Ponceau S staining prior to excision. From 193 plates (24.5 cm×24.5 cm), approximately 5-7 µg of p107 were purified.

In further detail, cells from approximately fifty confluent plastic plates (24.5 cm×24.5 cm; Nunc) of 293 cells were harvested by scraping into TBS (10 mM Tris-HCl, 150 mM NaCl) and collected by centrifugration. After removal of the supernatant, cells were lysed in 80 ml of ice cold lysis buffer (50 mM Tris-HCl, pH 8.0, 170 mM NaCl, 0.5% (v/v) NP-40, 10 µg/ml aprotinin [Sigma], phenylmethylsulfonyl-fluoride ["PMSF", Sigma], leupeptin [Boehringer-Mannheim] for 30 min. The lysate was cleared by centrifugation. The cleared lysate was incubated with approximately 2 ml of MAb M73 (anti E1A, described in Harlow et al., J. Virol. 55:533-546, 1985) covalently crosslinked to protein A sepharose (Pharmacia) prepared generally as described in Harlow et al., Cold Spring Harbor Laboratory, 1988; Simanis et al., Virology 144:88-100, 1985; Ewen et al., Cell 58:257-67, 1989). The mixture was incubated with rocking for 5 hrs at 4° C. Immune complexes were washed first with approximately 350 ml 10 mM Tris-HCl (8.0), 250 mM NaCl, 1 mM EDTA, 0.5% NP-40, and loaded into an empty column. The loaded column was further washed with 10 mM Tris-HCl (8.0), 100 mM NaCl, 1 mM EDTA. Bound protein was eluted from the mAb M73-protein A sepharose column with 100 mM triethylamine, pH about 11, and fractions were collected. Aliquots of the fractions were analyzed by SDS-gel electrophoresis. Peak fractions for the p107 protein were pooled, dialyzed against several volumes of double distilled water at 4° C. The samples was then frozen in dry ice ethanol and lyophilized. The dried samples were resuspended in 62.5 mM Tris-HCl (6.8), 2% SDS, 4M urea, 5% β-mercaptoethanol, 0.01% BPB. The sample was incubated at 37° C. for several hrs, boiled and then spun in a microfuge prior to loading on a gel. After electrophoresis through a 6% gel the proteins were visualized by staining in 0.05% coomassie brilliant blue R-250. The band corresponding to p107 was excised, crushed, and soaked in a small volume of 62.5 mM Tris-HCl, 2% SDS, 5% β-mercaptoethanol for 4 to 5 hrs. The gel fragments were loaded onto a second 8% gel. After electrophoresis, the p107 protein was transferred to nitrocellulose in 25 mM Tris-HCl, 192 mM glycine, 2% methanol, 0.005% SDS, pH 8.3 (as described generally in Aebersold et al., Proc. Natl. Acad. Sci. USA 84:6970-74, 1987; Towbin, Proc. Natl Acad. Sci. USA 76:4350-54, 1979). Bound protein was stained in 0.1% Ponceau S, 1% acetic acid (Aebersold et al., 1987) for 20 to 30 sec and destained in H₂O. The stained p107 band was excised. A total of 193 plates of 293 cells were processed. About 7 µg of purified p107 was obtained. The total area of nitrocellulose used for subsequent protein sequencing was approximately one square cm.

Isolation and Sequence of Peptides

N-terminal sequences of several tryptic peptides of p107 were obtained by automatic sequenation. The peptides were isolated by HPLC after in situ tryptic digestion of gel band purified and blotted p107.

In detail, in situ tryptic digestion of the p107 electroblotted onto nitrocellulose was performed generally as described in Aebersold et al., 1987, omitting the NaOH wash to minimize loss of protein. Sequencing grade bovine trypsin was from Boehringer Mannheim. After digestion the solution was immediately stored at −20° C. until separation of the resultant peptides by narrowbore reverse-phase PHLC was carried out.

Peptides were separated by narrowbore reverse phase HPLC in a Hewlett-Packard 1090 HPLC equipped with a 1040 diode array detector, using a Vydac 2.1 mm×150 mm C4 column. The gradient employed was a modification of that described by Stone et al., Techniques in protein Chemistry, Academic Press, Inc., 1989. Briefly, where buffer A was 0.06% trifluoroacetic acid/H₂O and buffer B was 0.55% trifluoroacetic acid/acetonitrile, a discontinuous gradient of 5% B at 0 min, 33% B at 63 min, 60% B at 95 min and 80% B at 105 min with a flow rate of 150 µl/min was used. Chromatographic data at 210 nm and 277 nm, and UV spectra from 209 nm to 321 nm of each peak were obtained. While monitoring absorbance at 210 nm, peaks were manually collected into 1.5 ml microfuge tubes and immediately stored without drying at −20° C. in preparation for peptide sequence analysis.

Samples for amino terminal sequence analysis were applied directly to a polybrene pre-cycled glass fiber filter and placed in the reaction cartridge of an ABI Model 477A protein sequencer. The samples were subjected to automated Edmann degradation using a program known as "NORMAL-1", which can be obtained from Bill Lane at the Harvard Microchemistry Laboratory, modified using the manufacturer's recommendations for faster cycle time (37 min) by decreasing drydown time and increasing reaction cartridge temperature to 53° C. during coupling. The resultant PTH amino acid fraction were manually identified using an on-line ABI model 120A HPLC and Shimadzu CR4A integrator.

Molecular Cloning of the T/E1A Associated p107 Protein

From the partial sequences of three peptides underlined in FIGS. 1.1-1.3 and labeled as NT65, NT85 and NT104, variously long, and moderately degenerate (for NT65) and non-degenerate (for NT85 and NT104) oligonucleotides encoding these three sequences were constructed using the codon utilization tables of Lathe, *J. Mol. Biol.* 183:1-12, 1985. These oligonucleotides were used to screen a newly generated cDNA library from 293 cells, and a number of cross hybridizing positives were identified. The largest clone isolated was 5.5 kb.

Construction of the cDNA library and screening was carried out as follows. Total cellular RNA was prepared from 293 cells (Maniatis et al., 1982). Poly A RNA was prepared using an oligo dT mRNA purification column (Pharmacia). The poly A RNA was used to constrast a directionally cloned cDNA library in Uni-Zap (Stratagene) following the manufacturer's instructions. DNA was packed using Strategene's Gigapack II Gold Packaging extract.

The unamplified library was screened with $^{32}P$-labeled oligonucleotides. From the three peptide sequences NT65: LTAQANVEYNLQQHFEK; NT85: EYEEYVLTVGDFDE; and NT104: VTIPLH-GVANDAGEITLIP the following oligonucleotides were respectively constructed: 5' GAGGC(T-C)AATGTGGAGTA(TC)AACCTGCAGCAGCA(TC)TTTGAGAA3'; 5' AATTCTCAT-CAAGTCGCCCACTGTCAGCACATA CTCCTCATACTCG 3' (the AATT at the 5' end and the G at the 3' end were incorporated into the oligonucleotide to facilitate cloning); and 5' AATTCGG-GGATCAGGGTGATCTCGCCAGCATCATTGG-CCAGCCATGC AGGGGGATGGTCACG 3' (the same flanking sequences found in the second oligonucleotide were also engineered into this oligonucleotide).

Filters were hybridized with about $3 \times 10^6$ cpm/ml for each oligonucleotide in 6X SSC, 5X Denhardt's, 20 mM NaPO4, 20% formamide, 0.1% SDS and 100 μg/ml denatured, sonicated salmon sperm DNA at 42° C. for 12-18 hrs. Filters were washed in 0.2X SSC at 60° C. and then autoradiographed. Hybridizing phage were plaque purified. The plasmid, pBluescript SK(−), containing the cloned insert, was generated by in vivo excision and recirculatization using the purified phage following the protocol provided by Stratagene. This DNA was used for further analysis.

In Vitro Transcription and Translation

Cloned inserts in the pBluescript SK(−) or pBluescript II SK(−) plasmid were used in vitro transcription reactions using T3 polymerase (Pharmacia). Transcription and translation reactions were performed as described in Kaelin et al., *Mol. Cell. Biol.* 10:3761-69, 1990.

When used as a template for in vitro transcription-translation, several products were identified. The largest was about 100 kd, and the smallest was about 36 kd, as appears in FIG. 4. Partial proteolytic digests of the 100 kd product and of intact p107 isolated from 293 cells revealed the same pattern of peptide products, indicating that the cDNA template encodes p107. Moreover, all translation products of greater than 48 kd size bound to T and to E1A but not to a non p107-binding T mutant, K1T, in immunoprecipitation assays, indicating that the products of this cDNA retain the T/E1A binding activity of the authentic, in vivo-synthesized product. In these gels, authentic p107 migrated just above the 116 kd marker (see, Ewen et al., 1989), suggesting that the 100 kd translation product might be missing certain p107 sequences.

When used as a probe in a northern blotting experiment in which poly A-containing RNA from 293 cells was analyzed, a prominent 5.9 kb RNA species was identified, as FIG. 5 shows. Other less well-defined minor species were also detected. These data are consistent with the major species being a prominent p107 mRNA. Experiments performed on monkey cells indicate that p107 exists as a family of closely migrating bands.

p107 Binding Assays

Binding of in vitro translated p107 to T and to E1A was assayed generally as described for RB. The mouse cell lines MEFψpPV-0 and MEFψK1 (Chen et al., *J. Virol.* 64:3350-57, 1990) were used as sources of T and K1 respectively. The cell line 293 was used as a source of E1A.

Peptide Map

One dimensional chymotryptic mapping was performed generally as described in Ewen et al. 1989.

PCR Subclone of p107 cDNA

To generate a cDNA of p107 starting at methione 57, an oligonucleotide incorporating a consensus start for translation and p107 sequences (5' GCGCGGATCCG-CCACCATGATTGGGGATGACTTAG 3') and an oligonucleotide complementary to the T7 promoter element in pBluescript SK(−) (5' AGTGGGATC-CAATACGACTCACTATAGG 3') were used in a PCR reaction. PCR was performed generally as described in Kaelin et al. 1990, except that an annealing temperature of 55° C. was used. The PCR product was digested with BamHI and XhoI and subcloned into pBluescript II SK(−) digested with the same restriction enzymes. The resultant subclone was used for in vitro transcription and translation reactions as described above. DNA sequencing was performed according to the method described in Sanger et al., *Proc. Natl. Acad. Sci. USA* 74:5463-67, 1977.

The cDNA sequence and the predicted amino acid sequence of the clone encoding the p107-related 100 kd protein are shown in FIG. 3.1-3.3. Both strands of subclones of this master cDNA clone were sequenced, and the results were in full agreement. An open reading frame of 2805 bp extends from nt 1 to a stop codon at nt 2806. The same stop codon was found to be present in the same location and confirmed to be functional in three independent p107 clones and by in vitro translation of a truncated cDNA derivative of NT. Several p107 clones shared the same 3' end as determined by restriction analysis, suggesting that it denotes the natural 3' end of the cDNA. Since the distance from the stop codon to the 3' end is 2.7 kb, the gene contains a relatively long 3' untranslated region.

The cDNA segment encoding the 100 kd band is not likely to be a full length p107 cDNA for a number of reasons. The methionine codon at position 57 is not imbedded in a region predicted to be a good consensus start signal (see, Kozak, *J. Mol. Biol.* 196:947-50, 1987). Translation initiation at methionine 57 resulted in the synthesis of the 100 kd band, and the native protein migrates as a 120 kd band. While the difference in gel migration could be the result of a covalent modification of the latter, translation beginning at methione 57 led to the synthesis of a protein of the predicted size, again suggesting that the 100 kd protein lacks certain N-terminal sequences. In this regard, the sequences 5' to those encoding the methionine at position 57 are completely open and in frame with the p107 product sequence. Moreover, analysis of the codon usage in the region preceding this methionine residue suggests that it is likely to be the coding sequence. Taken together, these data suggest that the largest available clone is nearly, but not entirely, full length.

In an effort to detect the 5' end of the natural mRNA, a $^{32}P$ labeled oligonucleotide complementary to the thirty nucleotides at the 5' end was used as primer for primer extension. The results were consistent with the 5' end of NT being approximately 300 bp from the natural 5' end of the RNA.

Comparison of the p107 Sequence with the RB Sequence

When the predicted amino acid sequence of RB was compared to the available sequences of all proteins in the databases searched, no significant homologies were found (Lee et al., *Science* 235:1394-99, 1987, Friend et al., *Proc. Natl. Acad. Sci. USA* 84:9059-63, 1987). When the predicted amino acid sequence of p107 was compared to available sequence databases (three different gene banks), no significant homologies were found except for the existence of major elements of homology to RB.

Comparisons of the predicted p107 and human and murine RB sequences revealed extensive homology between p107 and both RB species, as shown in FIGS. 2.1 and 2.2. Seven regions of p107-RB homology were found. Comparing the two proteins linearly in the N to C direction, and referring to FIG. 2.1, the first homology region (40% identity) extends from residues 40 to 74 in p107 and 190 to 224 in RB. Then, three closely spaced (the spaces are fewer than 20 residues in length) regions of homology spanning amino acids 252-451 in p107 and covering amino acids 373-579 in RB were detected. The homology ranged from 35-52%, depending upon which region was analyzed. After a gap of about 200 residues in p107 and 60 residues in RB, three additional regions of homology spanning amino acids 648-816 in p107 and amino acids 640-771 in RB were also found. There was a gap of 46 residues between the second and the third region in p107. The corresponding gap in RB was 6 residues. The extent of homology among these three regions ranged from 38% to 62%. The human and mouse RB proteins show 91% identity. Thus, it was not a surprise to note that each of the human RB-human p107 homology regions corresponded precisely to a mouse RB-human p107 homology region. Furthermore, each pair of identical residues detected in p107 and human RB was repeated in the comparison of p107 and mouse RB.

The similarities between p107 and RB are most striking in view of what is known about the functional domain structure of RB. Hu et al., *EMBO J.* 9:1147-55, 1990, Kaelin et al., and Huang et al. *EMBO J.* 9:1815-22, 1990, have defined the minimal region of RB necessary for T and E1A binding as a colinear region extending from residues 379-793. We have termed it the "pocket" region of the protein (Kaelin et al., 1990, *Cell* 64:521-32, 1991). Two subsegments (A and B) composed of sequences which cannot be invaded by deletion mutagenesis without interrupting T/E1A bending function were also detected (Hu et al., 1990, and Huang et al., 1990). The approximately 75 residue region between them could be invaded, so long as the deleted residues were replaced with other non-specific sequences (Hu et al., 1990). Region A extends from residues 393/394 to 572/571 and Region B from residues 646/649 to 772/773. The p107 homology regions in RB exist almost completely within the RB pocket and correspond closely to both the A and the B regions. They do not overlap the above-noted spacer region, although the p107 homology region extends approximately 20 amino acids N terminal to the upstream boundary of the minimal RB pocket region. Analogous results were noted when the RB homology regions in p107 were mapped. Two segments homologous to the A and B subdomains of RB were noted in p107 but in p107 there is a much larger spacer region noted (about 200 residues in p107, compared to about 60 residues in RB).

At the DNA level, there was little siginficant homology between RB and p107. Some homology was detected at the 5' ends of the regions encoding segments A and B in both proteins. No stretches of identity greater than six nucleotides were detected.

Chromosome Mapping

A 4.4 kb cDNA clone was used for mapping by in situ hybridization with a digoxygenin-labeled probe. Hybridization procedures were essentially as described in Lawrence, *Cell* 52:51-61, 1988, *Science* 249:928-32, 1990. Analyses were performed on metaphase spreads of normal peripheral blood lymphocytes prepared by standard procedures. Slides were stored at −80° C. and were UV-treated (365 nm) for 1 hr and baked at 65° C. for 4 hrs just prior to hybridization. After rinsing in 1×PBS, slides were denatured in 70% formaldehyde/2×SSC for 2 min at 70° C., and then dehydrated in a graded series to 100% ethanol before air drying. Probe, previously labelled by nick-translation with digoxygenin dUTP (Boehringer), was denatured and combined with the hybridization solution at a concentration of 5 μg/ml. An excess of human Cot-1 DNA (BRL) was added to complete out hybridization to repetitive sequences, a step found necessary with this cDNA probe.

Following overnight incubation at 37° C., slides were rinsed three times for 30 min each and hybridization detected using anti-digoxygenin antibody directly conjugated to fluorescein (Boehringer). Metaphase chromosomes were identified by banding with DAPI (diaminophenylindole) enhanced by prior incorporation of 5-bromodeoxyuridine into chromosomal DNA.

In some instances simultaneous hybridization to p107 and to the placental tyrosine phosphatase gene (PTP1B) were performed using 2-color detection of bionine and digoxygenin labeled probes. The conditions used for this double-label hybridization are described in Johnson et al. GATA 8: In Press, 1990. Use of a dual-band optical filter allowed the two sequences to be visualized simultaneously in precise register with respect to one another.

The RB Homology Region in p107 Constitutes a "Pocket" Domain

In an effort to determine whether the A-Spacer-B region of p107 could operate independently in T-p107 and E1A-p107 binding, appropriate deletion mutants were generated. These proteins were produced by in vitro transcription and translation. Upon mixing with wild type and mutant species of T and with wild type E1A, co-immunoprecipitation of the relevant p107 fragment was sought after adding the relevant monoclonal antibodies.

The segment of p107 extending from one end of the RB homology region to the other bound successfully to T and to E1A, but not to the K1 mutant of T, which cannot bind either to RB or to p107 in vivo. Therefore, the 225 to 816 region of p107 constitutes an independent T/E1A binding domain, which we term the "p107 pocket".

The spacer region between subdomains A and B in the RB pocket is apparently ephemeral to the T/E1A binding function of this domain. The same is true for the putative p107 spacer. Specifically, the 75 residue RB spacer was substituted for the 205 residue p107 spacer, as shown in FIG. 3, and the resulting chimera was tested for T/E1A binding. The recombed chimaeric p107 segment was apparently as active in T and E1A binding as was the native p107 element. Moreover, the chimaeric p107 segment failed to bind to K1T. Thus, the p107 spacer, as identified by homology analysis, is not essential to at least one function of the p107 pocket, namely, the T/E1A binding function.

The recombined chimaeric p107 segment containing the RB spacer does not bind Cyclin A; the p107 spacer alone does bind Cyclin A.

Thus the in vitro binding studies demonstrate that only a fraction of the p107 primary sequence is necessary for the binding of T and E1A. Though the region in p107 necessary for T and E1A binding has not been mapped, the sequence similarity between the p107 sequences and the region in RB known to be involved in T/E1A binding is striking. The homology spans the two regions A and B defined as the minimal T and E1A binding region in RB as defined by Hu et al., 1990, Huang et al., 1990, and Kaelin et al., 1990. With the exception of the N termini of the A region the boundaries of the homology are fairly well confined to the T/E1A binding regions.

As pointed out above, the sequences between the two regions A and B of the pocket is not critical for T/E1A binding. Some space between the two regions is required, however. It is noteworthy that the spacing of the homology regions in p107 is considerably larger, about 205 amino acids, compared to about 75 amino acids in RB.

The sequence similarity between RB and p107 in the region of the pocket is consistent with the genetic analysis of T/E1A binding and peptide competition studies (De Caprio et al., *Cell* 58:1085-95, 1989; Dyson et al., *Cell* 58:249-55, 1989a; Ewen et al., 1989; Whyte et al., *Cell* 56:67-75, 1989). Moreover, recent evidence strongly suggests that the 300 kd E1A binding protein (Yee et al., *Virology* 147:142-53, 1985; Harlow et al., *Mol. Cell. Biol.* 6:1579-89, 1986) has a similar function. p300 may contain a colinear domain responsible for binding T and E1A that it structurally and functionally related to the RB and p107 pockets.

Every reported naturally occurring mutation in RB maps to the region necessary for T/E1A binding. Furthermore for those tested each fails to bind to T and E1A. Whether this region of RB is a hotspot for recombination or whether such mutations confer a growth advantage to these cells is unknown. Such mutations in the T/E1A binding region of p107 may confer a growth advantage to cells and give rise to human cancer.

In this regard Kaye et al. *Proc. Natl. Acad. Sci. USA* 87:6922-26, 1990 describes a point mutation (706, C→F) in RB isolated from a small cell lung carcinoma which inactivated RB function with respect to phosphorylation, in addition to its ability to bind T/E1A and the cellular proteins identified by Kaelin et al. 1990. This cysteine in RB is within a region of homology between RB and p107, and furthermore this amino acid is conserved between the two proteins in this region. A corresponding C→F mutation in p107 results in a mutant p107 that does not bind T.

An apparently normal p107 is present in the retinoblastoma cell line WERI-1 as well as a number of other Rb- cell lines; WERI-27Rb, SAOS-2 and NCI-H69. Thus, any growth suppression function of p107 is not acting redundantly to the growth suppression function of RB. The sequences of p107 confirms our earlier statement that p107 is not the product of the RB gene (Ewen et al, 1989; Dyson et al, 1989).

In this regard, at least eight cellular proteins can be found in a complex with RB, and the region of RB necessary for binding T or E1A was also responsible for binding to the cellular proteins. The binding of RB to the cellular proteins is capable of being competed for by T peptide, and a variety of RB mutants did not bind to the cellular proteins.

The same set of cellular proteins that have been shown to bind RB also bind p107. At present it is unclear whether either p107 or RB works upstream or downstream of the cellular proteins in RB mediated growth suppression. The sequence similarity between p107 and RB, the genetics with respect to T/E1A binding, and the fact that peptide replicas can abolish the interactions of p107 and RB with T/E1A and with cellular proteins suggests that the cellular proteins are working upstream of p107 and RB, and suggests that p107 has effector functions different from RB. Alternatively (but apparently unlikely), RB binding to these cellular proteins may not alone be sufficient for it to mediate its growth suppression function. At present we know little about the functions of the sequences outside of the RB pocket which comprise 60% of the protein, and it is noteworthy that some homology exists between portions of the N termini of RB and p107. Sequences outside the pocket may modulate binding of the cellular proteins to pocket during the cell cycle.

Studies of the phosphorylation status of p107 throughout the cell cycle can provide clues as to when in the cell cycle it exerts its growth suppression function. It has been proposed, on the basis of such studies, that RB may be involved in the G1/S transition or entry into G0. p107 exists in both phosphorylated and unphosphorylated forms, and T (but not E1A) binds only to the unphosphorylated form of p107.

Use

The invention provides for early diagnosis of neoplasm by detection of an absence of wild-type p107 genes, or by detection of the presence of non-wild-type p107 genes, in a tissue sample from the subject, using techniques well-known in the art.

For example, the invention may be used to diagnose tumorigenicity in a tissue sample resulting from point mutations or specific deletions in the p107 gene. Point mutations in the p107 gene sequence may be detected by cloning and sequencing the p107 allele present in tumor tissue. If desired, a polymerase chain reaction technique may be used to amplify the signal of the target gene sequence. Point mutations in the p107 gene sequence may also be detected by cloning the mRNA isolated from tumor tissue to produce cDNA, then sequencing the resultant cDNA, or by sequencing the mRNA directly.

Another method traditionally used to detect point mutations is mismatch detection. This technique uses a labeled riboprobe (sense or anti-sense) which is complementary to the wild-type p107 gene sequence. The riboprobe is first annealed to either mRNA or DNA isolated from tumor tissue, then cleaved with RNase. The resultant preparation is separated on an electrophoretic gel, and mismatches cleaved by the RNase are detected as smaller segments than the full-length duplex RNA, made up of the riboprobe and p107 mRNA or DNA sequence.

Similarly, mismatches can be detected using DNA probes. Previously identified mutations in the p107 gene may be detected using allele-specific probes containing a gene sequence corresponding to that mutation. Presence of a specific mutation is confirmed when an allele-specific probe hybridizes with DNA sequences from the tumor tissue, which may be amplified using a polymerase chain reaction technique.

Specific deletions of the p107 gene may be detected using restriction fragment length polymorphisms probes, directed at either the p107 gene itself, or nearby marker genes. This invention may be used to detect deletions of the entire p107 gene through the absence of expression products, including p107 mRNA or p107 protein. Loss or mutation of the p107 gene may also be detected through loss of the p107 protein functions, such as loss of the ability to bind SV40 large T antigen. A mutation in the genetic sequence may result in detectable alterations in the p107 protein structure, leading to an inability to bind SV40 large T antigen. Alterations in the p107 protein structure may therefore be detected through binding studies using SV40 large T antigen or monoclonal antibodies.

In addition to tumor tissue, mutations in the p107 gene or protein may be detected in serum, stool, urine, sputum or other body fluids. Diagnostic methods may be designed to employ one or more of these body samples, to detect carcinogenesis at multiple stages. Methods could be designed to detect predisposition to cancer, due to the loss of wild-type p107 alleles. The invention could also be used to facilitate early detection of tumors, or as a means of evaluating the progress of treatment, including chemotherapy and radiotherapy.

The detection of a p107 gene deletion may aid physicians in selecting a course of treatment, based on the presence or absence of the p107 sequence. Because the p107 gene is implicated in the development of a broad range of tumors, it may be used to detect numerous forms of carcinogenesis, including but is not limited to, breast and lung tumors, leukemia and osteosarcomas.

This invention may also be used to supply a p107 gene sequence where the wild-type allele has been mutated or deleted. The wild-type gene may be inserted into a defective cell using vectors well known in the art. If this process is employed, it is preferable to induce recombination of the mutant p107 gene with the wild-type gene in a manner such that the mutant gene is corrected. Alternatively, polypeptides or molecules with p107 activity may be introduced into the defective gene through microinjection to supply the missing wild-type p107 protein product.

The observation that the p107 gene maps to a segment of 20q11.2 suggests a possible specific role for p107 as a tumor suppressing element. Approximately 1–6%, at a minimum, of patients having a neoplastic disease of myeloid cells have a cytogenetically detectable deletion of 20q, as described in Davis et al., *Cancer Genet. Cytogenet.*, 12:63–67, 1984. Yunis et al., *Brit. J. Haematol.*, 68:189–94, 1988, reports that the tumor cells from 35% of patients having myelodysplastic syndrome showed a deletion of 20q; approximately 21% of patients having acute myelogenous leukemia also showed this deletion. In the majority of myelodysplastic patients showing the deletion, the deletion has been described as a terminal deletion with variability in the breakpoint within band q11, which results in a loss of all DNA terminal to the breakpoint. Le Beau et al., *Proc. Nat. Acad. Sci., USA*, 82:6692–96, described detecting a smaller, less frequent 20q deletion between breaks at 20 q11.2 and 13.1. Taken together, these data and the similarities between p107 and RB suggest that p107 can play a role in the evolution of one or more neoplastic disorders of myeloid cells. p107 loss may be a relatively frequent event in human tumors, as is true of RB.

Because RB and p107 may exhibit certain redundant functions, and because a loss of both p107 and RB can be lethal, tumors in which RB function is lost can be expected to have retained p107 function, and vice versa.

We claim:

1. A cDNA encoding p107, comprising SEQ ID NO. 1.

2. A cell containing recombinant p107-encoding DNA, said p107 DNA comprising SEQ ID NO. 1.

3. A nucleic acid probe complementary to a human p107 gene.

* * * * *